United States Patent
Behm et al.

(10) Patent No.: US 11,796,523 B2
(45) Date of Patent: Oct. 24, 2023

(54) VAPOR AND PARTICULATE SENSOR SYSTEM FOR AEROSPACE

(71) Applicants: Gentex Corporation, Zeeland, MI (US); Vaporsens, Inc., Salt Lake City, UT (US)

(72) Inventors: Michael F. Behm, Zeeland, MI (US); Benjamin R. Bunes, Murray, UT (US); Douglas W. Later, Sandy, UT (US)

(73) Assignee: GENTEX CORPORATION, Zeeland, MI (US)

( * ) Notice: Subject to any disclaimer, the term of this patent is extended or adjusted under 35 U.S.C. 154(b) by 454 days.

(21) Appl. No.: 17/076,277

(22) Filed: Oct. 21, 2020

(65) Prior Publication Data
US 2021/0116432 A1   Apr. 22, 2021

Related U.S. Application Data

(60) Provisional application No. 62/923,871, filed on Oct. 21, 2019.

(51) Int. Cl.
*G01N 33/00* (2006.01)
*G01N 1/22* (2006.01)
*G01N 31/22* (2006.01)

(52) U.S. Cl.
CPC ....... *G01N 33/0031* (2013.01); *G01N 1/2226* (2013.01); *G01N 31/22* (2013.01); *G01N 33/0075* (2013.01)

(58) Field of Classification Search
CPC .. G01N 33/0031; G01N 1/2226; G01N 31/22; G01N 33/0075
See application file for complete search history.

(56) References Cited

U.S. PATENT DOCUMENTS

| | | | |
|---|---|---|---|
| 4,866,439 A * | 9/1989 | Kraus | G08B 17/117 244/1 R |
| 8,452,489 B2 | 5/2013 | Marra | |
| 10,043,363 B2 | 8/2018 | Riedel | |
| 10,329,022 B2 | 6/2019 | Fox et al. | |
| 2008/0283663 A1 | 11/2008 | Space et al. | |
| 2017/0067849 A1 | 3/2017 | Cobianu et al. | |
| 2017/0122893 A1 | 5/2017 | Wang et al. | |
| 2018/0080891 A1 * | 3/2018 | Potyrailo | G01N 27/04 |
| 2018/0082558 A1 | 3/2018 | Riedel | |
| 2018/0148182 A1 | 5/2018 | Fagundes et al. | |

FOREIGN PATENT DOCUMENTS

| | | | |
|---|---|---|---|
| CN | 104267068 A | 1/2015 | |
| KR | 100743251 B1 | 7/2007 | |
| WO | WO-2012023136 A1 * | 2/2012 | G01N 33/00 |

* cited by examiner

*Primary Examiner* — Benjamin R Schmitt
(74) *Attorney, Agent, or Firm* — Price Heneveld LLP; Brian James Brewer (57) ABSTRACT

A detection system for an aircraft that includes at least one chemical sensor or an array of nanofiber chemical sensors for sensing an airborne material. The chemical sensor has an electrical characteristic that changes in the presence of the airborne material. The system further includes a processor coupled to the chemical sensor. The processor monitors electrical characteristic of the chemical sensor and generates a detection signal in response to a change in the electrical characteristic.

16 Claims, 5 Drawing Sheets

VAPOR AND PARTICULATE SENSOR SYSTEM FOR AEROSPACE

CROSS-REFERENCE TO RELATED APPLICATIONS

This application claims priority under 35 U.S.C. § 119(e) and the benefit of U.S. Provisional Application No. 62/923,871 entitled VAPOR AND PARTICULATE SENSOR SYSTEM FOR AEROSPACE, filed on Oct. 21, 2019, by Michael F. Behm, the entire disclosure of which is incorporated herein by reference.

TECHNOLOGICAL FIELD

The present invention generally relates to a chemical detection system and, more particularly, to vapor and particulate sensors configured to detect a chemical presence in an aircraft.

BACKGROUND OF THE INVENTION

Identification and detection of materials in an aircraft is a significant security concern. The disclosure provides for a vapor and particulate sensor system that may be utilized to detect chemical compositions in an aircraft.

SUMMARY

In one aspect of the disclosure, a detection system for an aircraft comprises at least one chemical sensor for sensing an airborne material. The chemical sensor has an electrical characteristic that changes in the presence of the airborne material. The system further comprises a processor coupled to the chemical sensor. The processor monitors the electrical characteristic of the chemical sensor and generates a detection signal in response to a change in the electrical characteristic.

In another aspect of the disclosure, a method for sensing an airborne material in an aircraft is disclosed. The method comprises monitoring electrical characteristics detected by a plurality of chemical sensors forming a plurality of air quality sensors. The plurality of air quality sensors are disposed in a plurality of detection zones distributed throughout the aircraft. The method further comprises sensing an airborne material in one of the detection zones in response to a detection signal communicated from one of the air quality sensors and identifying an affected zone of the plurality of detection zones in which the airborne material is detected in response to the detection signal communicated from one of the air sensors. The method further comprises outputting a status indication identifying the affected zone in response to the identification of the affected zone and the airborne material.

In yet another aspect of the disclosure, a detection system for an aircraft is disclosed.

The system comprise a plurality of chemical sensor modules disposed in a plurality of compartments of the aircraft. The plurality of chemical sensor modules include a plurality of nanofiber chemical sensors configured to distinguish among a plurality of airborne materials in response to electrical characteristics detected by the plurality of nanofiber chemical sensors. A controller is in communication with the chemical sensor modules. The controller is configured to receive detection signals from the plurality of chemical sensor modules indicating a chemical presence in each of the plurality of compartments or zones in the aircraft. In response to the detection, the controller outputs a status indication indicating the chemical presence and the corresponding compartment or zone in the aircraft in which the chemical presence is detected.

These and other aspects, objects, and features of the present disclosure will be understood and appreciated by those skilled in the art upon studying the following specification, claims, and appended drawings. It will also be understood that features of each example disclosed herein may be used in conjunction with, or as a replacement for, features of the other examples.

BRIEF DESCRIPTION OF THE DRAWINGS

The following is a description of the figures and the accompanying drawings. The figures are not necessarily to scale, and certain features and certain views of the figures may be shown exaggerated in scale or in schematic in the interest of clarity.

In the drawings.

DETAILED DESCRIPTION OF THE PREFERRED EMBODIMENTS

It is to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise. As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Figure 1:
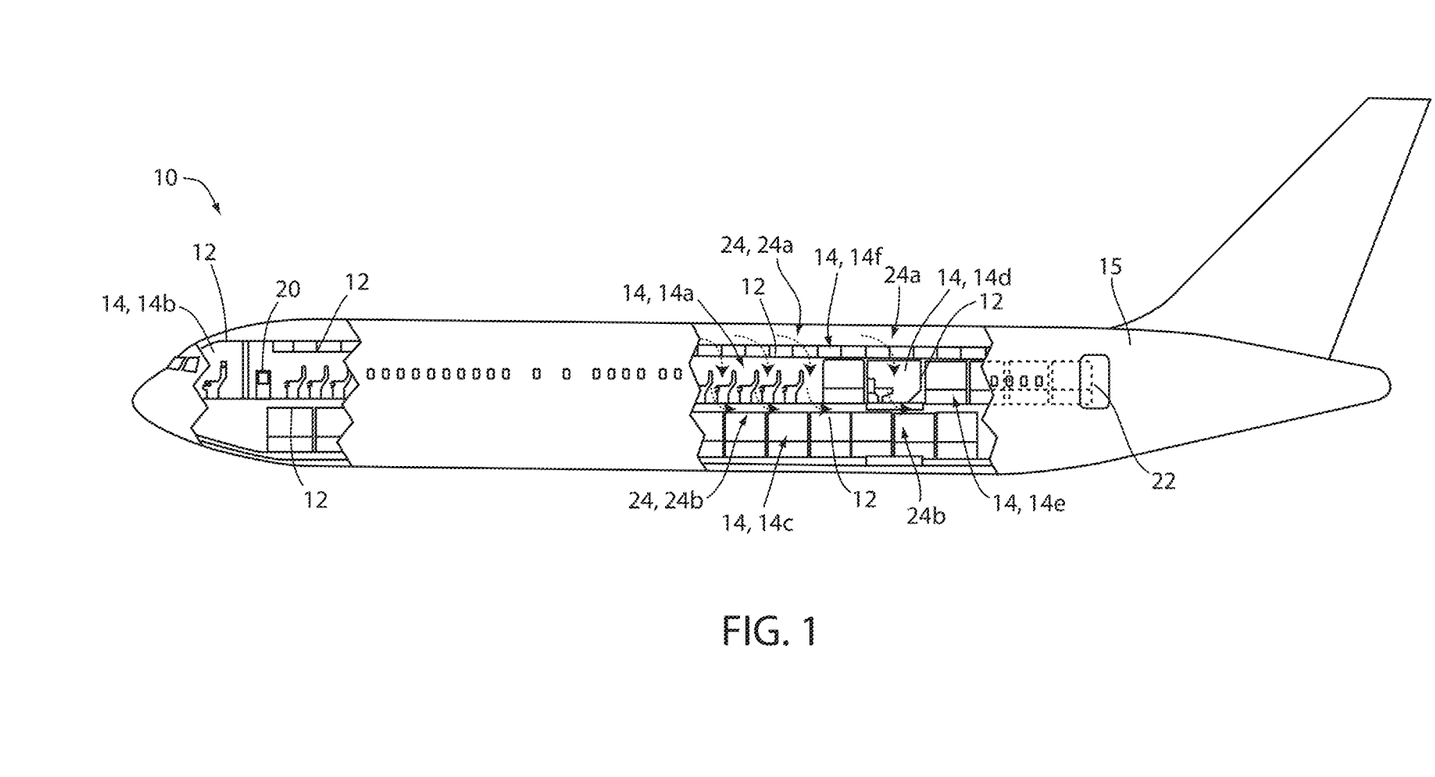
FIG. 1 is a cutaway view of an aircraft demonstrating a plurality of aircraft compartments.
Figure 2:
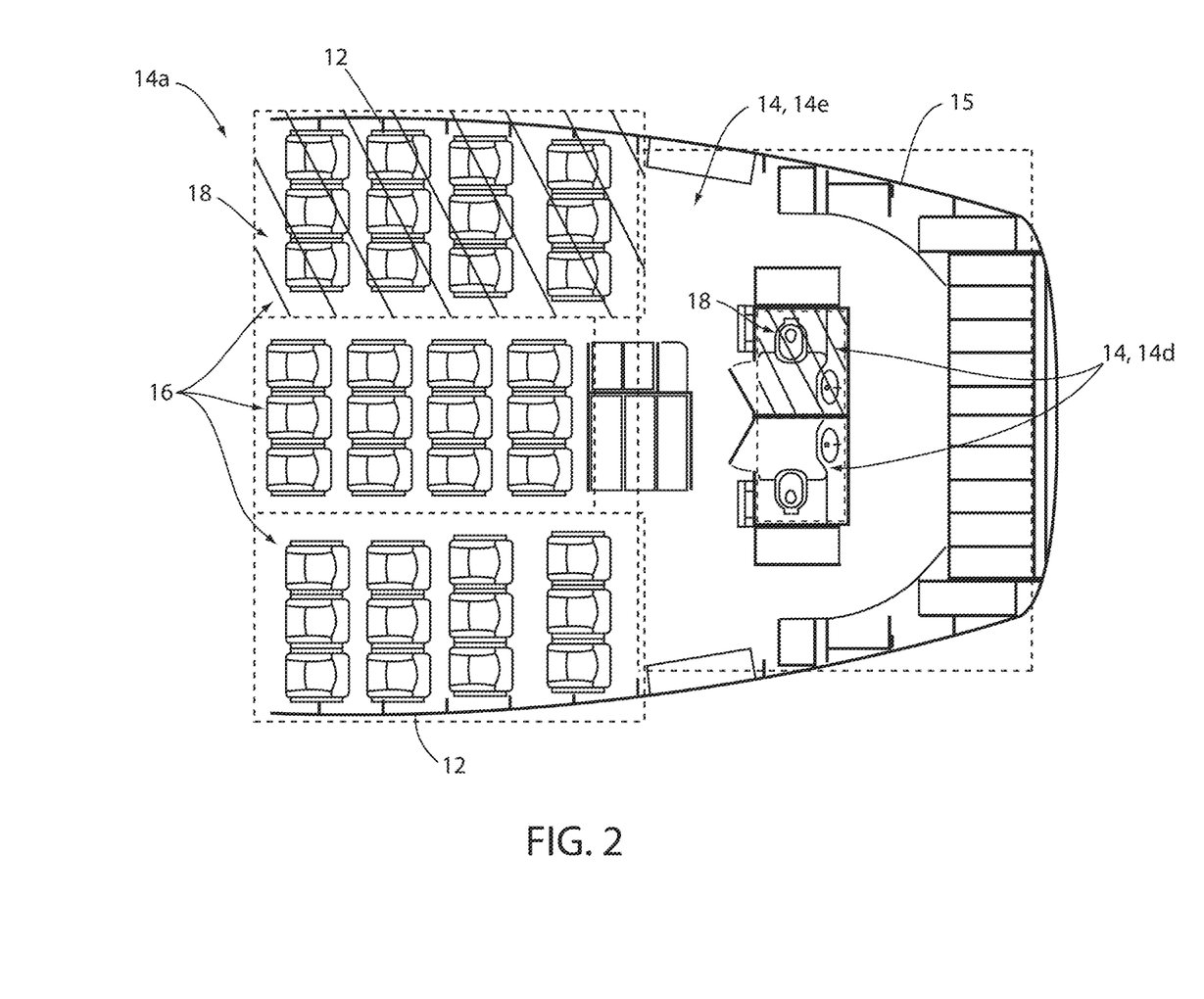
FIG. 2 is a plan view of a passenger compartment of an aircraft.

Referring now to FIGS. 1-2, reference numeral 10 generally designates an air quality detection system. The detection system 10 may comprise a chemical detection device or sensor 12, which may be designed to identify a type and/or concentration of various chemicals in one or more compartments 14 of an aircraft 15. In some examples, the detection device 12 may be incorporated in a ventilation system, which may comprise a plurality of ventilation zones distributed throughout a passenger compartment 14a. The aircraft 15 may further comprise a plurality of compartments including, but not limited to, a flight deck or cockpit 14b, a cargo hold 14c, a lavatory 14d, service area 14e, overhead compartments 14f, etc. As further discussed herein, the detection device 12 may be located in various compartments 14 and zones 16 that may further subdivide the compartments 14 of the aircraft 15.

In various embodiments, the chemical detection device 12 may correspond to a variety of sensory devices. For example, the chemical detection device 12 may be implemented by a variety of devices including, but not limited to, nanofiber-based chemiresistive sensors, nanomaterial-based sensors, electrochemical sensors, amperometric gas sensors, carbon monoxide sensors, catalytic bead sensors, thermal conductivity sensors, metal oxide sensors (MOS), infrared (IR) sensors, photoionization detectors (PID), etc. Such sensors may vary in application and, therefore, may be implemented in various combinations to achieve the identification and detection of various chemicals and contaminants that may be present in the passenger compartment. Though specific examples are discussed herein, the chemical detection device 12 may be implemented by similar sensors or developing sensory technologies without departing from the spirit of the disclosure.

As shown in FIG. 2, a plurality of chemical detection sensors 12 are distributed throughout the passenger compartment 14a, the service area 14e, and the lavatories 14d. As depicted, the detection sensors 12 may be located in detection zones 16 within one or more of the compartments 14. For example, the passenger compartment 14a may comprise a first zone 16a, a second zone 16b, a third zone 16c, etc. In this way, the system 10 may be configured to detect the presence of a chemical (e.g., a contaminant, allergen, contraband, substance, and/or particulate) and identify an affected or alert zone 18 via a status monitoring system 20 (FIG. 5) of the aircraft 15. In this way, the system 10 may be configured to detect the presence of one or more chemicals or contaminants in the aircraft 15 and identify a corresponding affected zone 18 of the zones 16 and/or compartments 14.

In addition to the detection of the presence of one or more chemicals or contaminants in the aircraft 15 in specific zones 16, the system 10 may be configured to detect the spread of a chemical or contaminant from one zone to another. For example, the system 10 may be configured to detect the spread of a chemical from the first zone 16a to the second zone 16b and track the affected zones chronologically over a temporal period. In this way, the system 10 may not only provide for the detection of a contaminant in each of the zones 16 but may also track an origin or first zone in which the contaminant is detected as well as each additional zone in a chronologically tracked sequence over time. Such a record may be stored in memory and may be implemented for troubleshooting or tracing passengers, luggage, containing, and various other compartments or containers from which the contaminant may have originated.

Though discussed in reference to the compartments generally accessible by passengers, the chemical detection sensors 12 and the corresponding detection zones 16 may be located within any of the compartments of the aircraft 15. Additionally, the corresponding detection zones 16 may vary in proportions, such that the corresponding regions of the aircraft 15 may be smaller depending on the desired configuration and location accuracy required to achieve the desired operation of the status monitoring system 20. Accordingly, the system 10 may be scaled or adjusted to suit a variety of aerospace applications including, but not limited to, commercial aircraft, passenger aircraft, recreational aircraft, etc.

In some implementations, the system 10 may comprise one or more of the detection sensors 12 located proximate to an entry region 22. In this configuration, the system 10 may be configured to detect the presence of one or more chemicals as the passengers or crew are boarding the aircraft 15. Additionally, the system 10 may be configured to monitor regions of the aircraft 15 where alcohol or other controlled substances should not be present or consumed. For example, detection sensors 12 may be distributed within the cockpit 14b for detection of chemicals that may suggest or indicate that one or more members of the flight crew is under the influence of or consuming a substance (e.g. alcohol). In this way, the system 10 may further provide for security related to the operation of the aircraft 15. As further discussed in reference to FIG. 5, a detection of a crew-related security issue may be communicated via a wireless communication interface to a central airline monitoring station or system.

Figure 5:
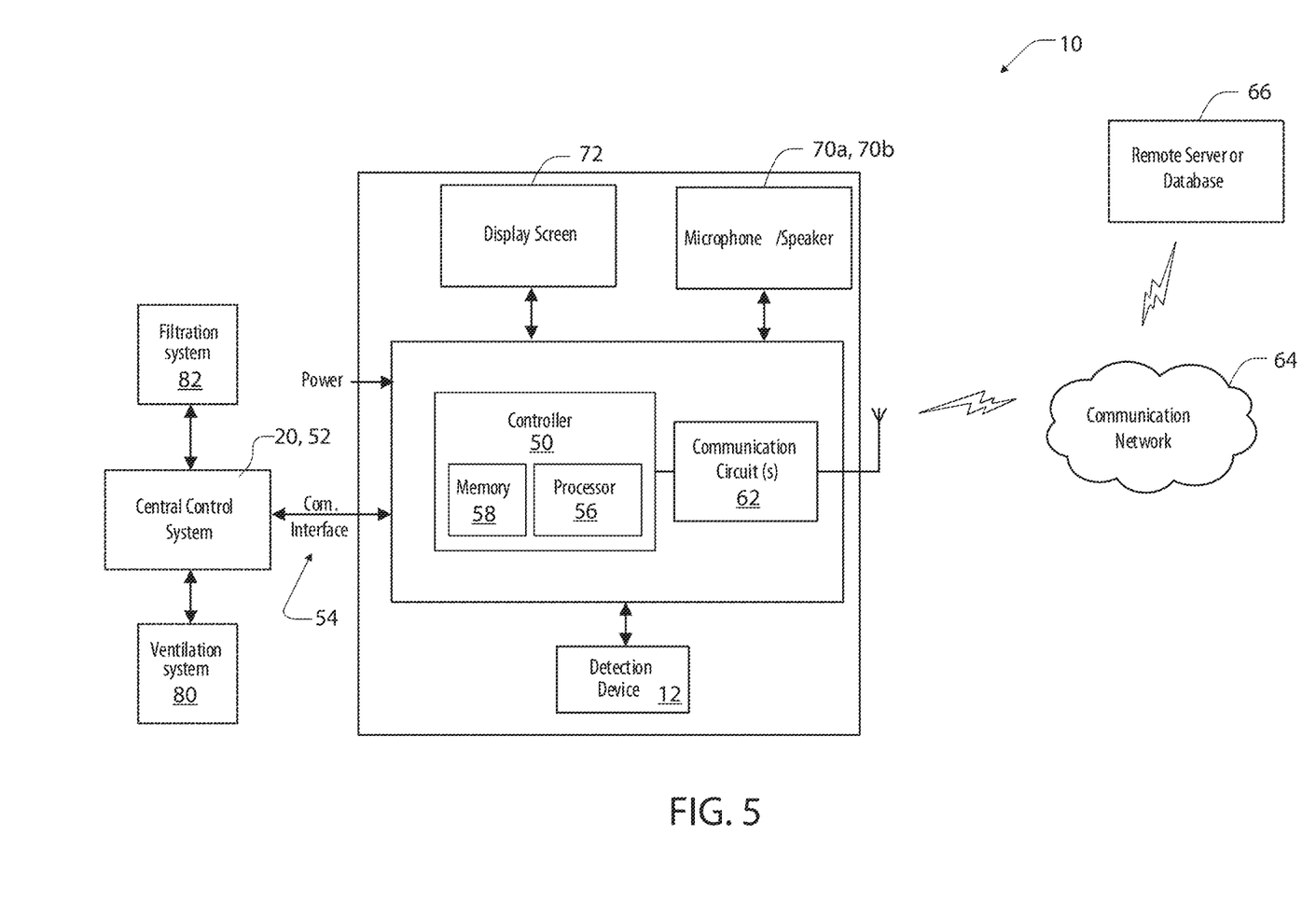
FIG. 5 is a block diagram of a chemical detection system comprising a chemical detection sensor in accordance with the disclosure.

Still referring to FIGS. 1 and 2, a plurality of ventilations zones 24 or air circulation zones 24 are shown. Each of the ventilation zones 24 may be supplied fresh air from the ventilation system 80 of the aircraft 15 (FIG. 5). The air supplied and/or returned to the ventilation zones 24 may be referred to herein as supplied air 24a or returned air 24b, each of which may be referred to as ventilation flows. The ventilation zones 24 may correspond to the detections zones 16 and comprise a chemical detection sensor 12 disposed in one or more of the supply or return ducts forming the ventilation zones 24. In this configuration, the chemical detection sensors 12 may be positioned in a plurality of ventilation flows of the ventilation system 80. In operation, detection signals from each of the corresponding chemical detection sensors 12 of each of the ventilation zones 24 may be supplied to a controller 50 of the system 10. In response to the detection signals, the controller 50 may identify the one or more contaminants in the ventilation zones 24 and the corresponding compartments 14 or zones 16 of the aircraft 15.

Figure 3:
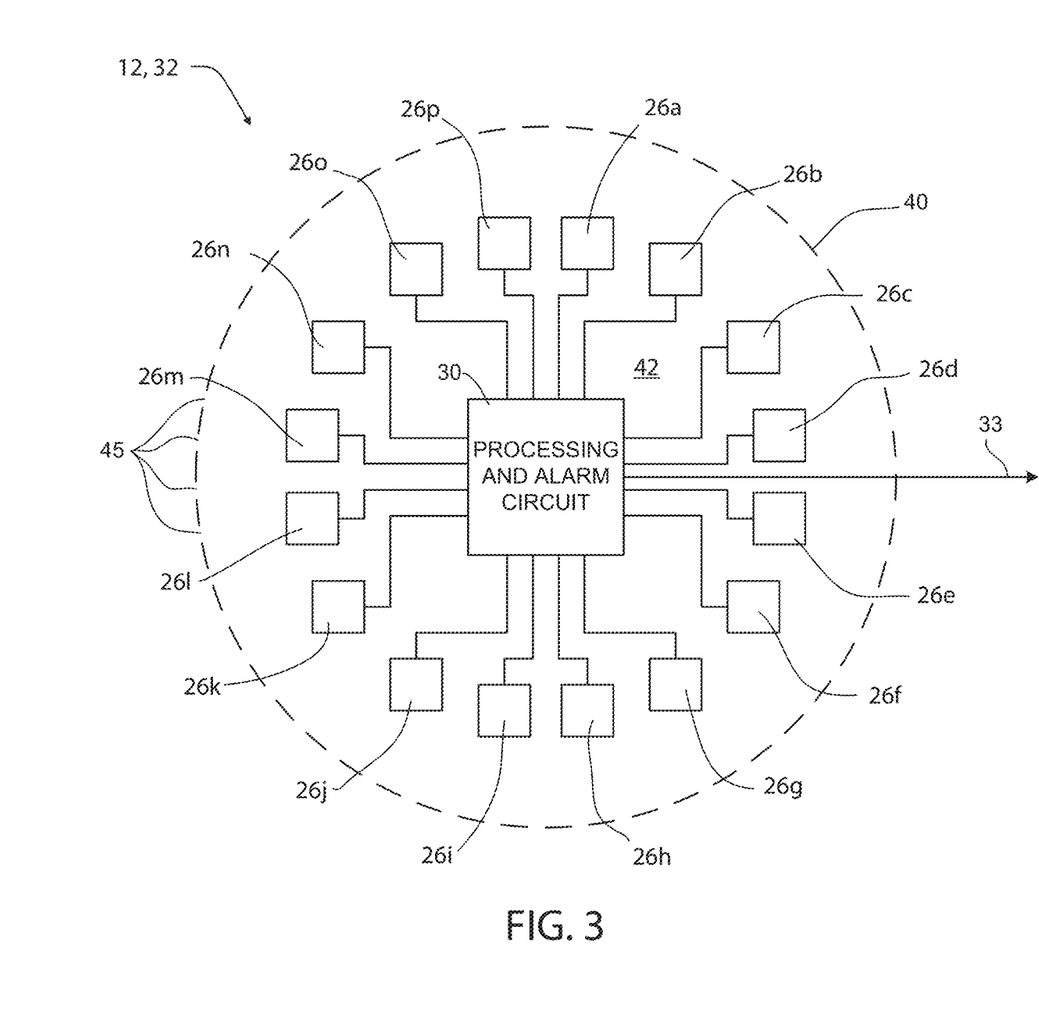
FIG. 3 is an electrical circuit diagram of a chemical detector.

Referring now to FIG. 3, an example of the detection device 12 is shown in communication with at least one nanofiber chemical sensor 26. The nanofiber chemical sensor 26 may be configured to sense various chemicals and compounds that may be present in the ambient air within the one or more compartments 14. In some embodiments, the at least one nanofiber chemical sensor 26 may comprise a plurality of nanofiber chemical sensors 26a-26p. In operation, each of the one or more nanofiber chemical sensors 26 may be in communication with a processor 30, which may be configured to monitor changes in electrical characteristics for each of the nanofiber chemical sensors 26 in the presence of the various airborne materials. Based on the combination of signals received from the at least one nanofiber chemical sensor 26, the processor 30 may be configured to identify the presence and concentration of one or more contaminants in the one or more compartments 14 or zones 16.

The nanofibers used in the sensors 26 may be synthesized with specific functional groups that can interact with specific airborne materials/vapors/particles. The nanofibers are deposited on an interdigitated electrode to form an electrode-nanofiber array 32. Interaction of the nanofibers with airborne materials changes the measured electrical characteristics of the nanofiber chemical sensor. An increase or decrease in the measured current or effective resistance of each of the nanofiber chemical sensors occurs as a result of interaction with these airborne material interactions.

Nanofibers of each of the sensors 26 with different functional groups have a different response to the same airborne material. By using the plurality of nanofiber chemical sensors 26 in an array 32, an identifying response signature can be established by the processor 30 for each of a plurality of airborne materials. Accordingly, based on the electrical signals communicated from the array 32, the processor 30 may be configured to detect a variety of conditions that may exist in the aircraft 15 and/or the one or more compartments 14. The nanofibers of the sensors 26 may have a proportionately large three-dimensional surface area that is resistant to particulate fouling. In various embodiments, the processor 30 may be configured to identify a variety of contaminants in the one or more compartments 14. In response to the particular contaminant or family of contaminants identified by the detection device 12, the system 10 may be configured to respond by outputting a variety of notifications and/or controlling a variety of systems of the aircraft 15.

In various embodiments, the detection device 12 may be configured to identify a variety of chemicals present in the passenger compartment and/or proximate to the aircraft 15. Chemicals and compounds that may be detected by the device 12 may be trained or programmed based on electrical signatures received by the processor 30 in response to the presence of the chemicals. Examples of chemicals that may be identified and/or detected may include, but are not limited to, Benzaldehyde, Hexane, Acetone, Ethanol, Diesel Fuel, Nitrobenzene, and Formaldehyde. Some examples of explosives and chemical agents that may be detected may include Nitromethane, DNT (Dinitrotoluene), TNT (Trinitrotoluene), ANFO (Ammonium Nitrate Fuel Oil), Ammonium Nitrate, PETN (may detect taggant), RDX (may detect taggant), TATP (Triacetone Triperoxide), H2O2 (Hydrogen Peroxide), TEP (Triethylphosphate), DMMP (Dimethyl methylphosphonate), 2-Chloroethyl ethyl sulfide, Triphosgene, Methyl Salicylate, sulfur mustard, sarin, tabun, cyclosarin, and VX. Some examples of toxic chemicals that may be detected by the detection device 12 may include, but are not limited to, Chlorine Gas, Ammonia, Hydrogen Peroxide, Sulfur Dioxide, Hydrochloric Acid, TEP (Triethyl Phosphate), Phosphine, Hydrogen Cyanide, Arsine, and Formaldehyde. The detection device 12 may also be configured to detect one or more narcotics, opioids, or illicit drugs including, but not limited to, heroin, pharmaceutical drugs OxyContin, Vicodin, codeine, morphine, methadone, and fentanyl, etc.

In some examples, the detection device 12 may also be configured to detect one or more chemicals commonly found in consumer foods and/or goods including, but not limited to, Trichloroanisole, Melamine, Trimethylamine, Limonene, Pinene, Linalyl Acetate, Menthol, Menthone, and Linalool. The device 12 may additionally be configured to detect various amines including, but not limited to, N-Methylphenethylam-lamine, Phenethylamine, Methylamine, Aniline, Triethylamine, and Diethylamine. Accordingly, based on the detection of each of the chemicals detected by the device 12, a controller or control system of the aircraft 15 may provide a corresponding response, which may mitigate an odor, deactivate a ventilation or accessory system, activate a call button, output a warning, and/or provide for a variety of beneficial system responses.

Figure 4:
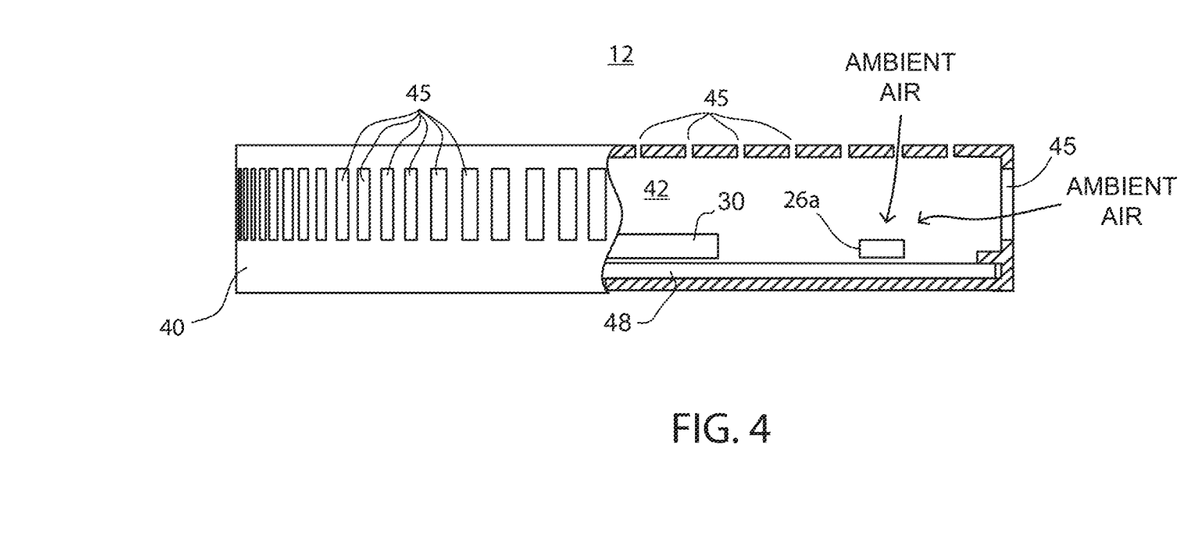
FIG. 4 is a side schematic view of the chemical detection device shown in partial cross-section.

Referring now to FIG. 4, the nanofiber chemical sensors 26a-26p of the detection device 12 may be arranged in any manner and may be disposed in an inner chamber 42 of a housing 40 having a plurality of air vents 45. The air vents 45 may provide for ambient and/or forced air to flow into the inner chamber 42. In this configuration, updated samples of the air present in the one or more compartments 14 may flow passed the nanofiber chemical sensors 26a-26p providing consistently updated monitoring of the chemical particulates present in the air. In various implementations, the air vents 45 may be large enough and/or numerous enough to allow the ambient air to flow into inner chamber 42 without restriction. The processor 30 may be in communication with various systems and/or controllers of the aircraft 15 via a connection 33. In various implementations, the connection 33 may correspond to a wired and/or wireless connection. Although the processor (i.e., Processing and Alarm Circuit) 30 and nanofiber chemical sensors 26a-26p are shown in FIG. 4 as being mounted on a common circuit board 48, they may be mounted on separate circuit boards.

Referring to FIG. 5, a block diagram of the system 10 comprising the detection device 12 is shown. The system 10 may comprise a controller 50 in communication with the detection device 12. The controller 50 may further be in communication with an aircraft control system 52 via a communication interface 54 of the aircraft 15. The communication interface 54 may be configured to deliver signals to the controller 50 identifying various states of the aircraft 15. For example, the controller 50 may be configured to control a variety of aircraft ventilation, filtration, alarm, and/or announcement functions via the communication interface 54. Such control signals may be submitted from the controller 50 to control various systems of the aircraft 15 via the communication interface 54 or any form of communication (e.g. wired, wireless).

The controller 50 may comprise a processor 56 having one or more circuits configured to control various operations of the system 10. The processor 56 may be in communication with a memory 58 configured to store instructions to control operations of the detection device 12. For example, the controller 50 may be configured to store one or more control responses configured to control various systems of the aircraft 15 in response to the detection of one or more chemicals by the detection device 12.

In some embodiments, the controller 50 may further comprise one or more communication circuits 62 configured to communicate via a communication network 64. Accordingly, the system 10 may be in communication with a remote server 66 (e.g. the central airline monitoring station or system) via the communication network 64. The communication network 64 may comprise one or more wireless or wired network interfaces or communication protocols. As discussed herein, wireless communication protocols may operate in accordance with communication standards including, but not limited to, ground air cellular towers; global system for mobile communications (GSM); code division multiple access (CDMA); Long Term Evolution (LTE or 4G LTE); satellite-based communications; and/or variations thereof. Additionally, each of the detection sensors 12 may be in communication with the system via a local wireless network or aircraft communication network. Accordingly, the controller 50 of the system may be configured to send an alert or message to the airline monitoring station or system device 68 and/or the remote server 66 identifying a detection of a chemical related to the operation of the aircraft 15 and/or a chemical present in the one or more compartments 14 or zones.

The system 10 may further be in communication with one or more of a microphone 70a and/or a speaker 70b. In such embodiments, the system 10 may be configured to communicate one or more warnings, instructions, and/or additional information to a user in response to the detection of one or more chemicals via the detection device 12. Additionally, the system 10 may be configured to initiate an emergency communication (e.g. a voice communication) from the aircraft 15 in response to the detection of a potentially hazardous chemical identified by the detection device 12. In some aspects, the controller 50 may further be in communication with a display screen 72, which may be disposed in various portions of the aircraft 15 (e.g., the cockpit 14b, service area 14e, etc.) for display of images and graphics, which may provide for the control to display instructions and/or warnings related to the detection of one or more chemicals by one or more of the detection devices 12 or the system 10.

Referring now to FIGS. 1, 2, and 5, various exemplary operations of the system 10 are discussed in reference to the examples provided herein. As generally discussed herein, the system 10 may provide for air quality monitoring within the one or more compartments 14 or zones 16 of the aircraft 15. Contaminants that may be detected in the one or more compartments 14 may be categorized generally as those that relate to passenger comfort related considerations (e.g. odors, perfumes, etc.) and those that relate to potentially dangerous chemicals. In operation, the controller 50 of the system may be configured to control a response of the system 10 to mitigate, control, ignore, and/or counteract the effects of various chemicals that may be detected by the detection device 12. In various examples, the controller 50 may be configured to control the system 10 to respond based on the specific type of chemical, a family of chemicals, and/or general category (hazardous versus non-hazardous) of the chemicals detected by the detection device 12. In this way, the controller 50 may be configured to provide a specific and/or configurable response to resolve the concerns related to the detection of specific chemicals and/or categories of chemicals.

Common chemicals and corresponding odors that may be detected by the device 12 may vary widely. For example, the device 12 may be configured to identify a variety of odors including, but not limited to, perfumes, feces, fish, skunk, pet odor, decaying biological material, methane, hydrogen sulfide, body odor (body-related bacterial odor), smoke, alcohol, bodily fluids, vomit, etc. Some of these odors may relate to comfort issues while others could present health issues to one or more passengers of the aircraft 15. Accordingly, the detection device may additionally communicate a concentration of the chemicals detected in the compartment 14 and zone 16 to the controller 50. According to the desired configuration, the controller 50 may respond to an indication of the presence of a chemical at a reported level in a variety of ways.

Additionally, the detection device 12 may be configured to detect and identify a variety of chemicals that may generally be considered dangerous which may or may not cause a significant odor. Examples of such chemicals or sources of such chemicals may be allergens including, but not limited to, peanuts, soy, perfumes, smog, etc. Additional examples of chemicals or sources of such chemicals may include, but are not limited to, explosives, gun powder, accelerants, carbon dioxide, carbon monoxide, volatile organic compounds (VOCs), chemical warfare agents (CWAs), toxic industrial chemicals (TICS), drugs (e.g. methamphetamine, cannabis, alcohol, etc.), smog, smoke, exhaust, etc. In response to the detection of such chemicals, the system 10 may respond in different ways, particularly in comparison to the detection of chemicals that may not be dangerous in relation the operation of the aircraft 15 or the health of passengers on the aircraft 15.

As discussed herein, the system 10 may operate in a passive configuration, wherein the controller 50 is configured to report the identification of chemicals via one or more alerts in the aircraft 15 (e.g. via indicators in the zones 16 or a monitor identifying detections in the zones 16) and/or communications to the remote server 66. In such embodiments, the system may communicate the presence of the chemicals to a user or administrator of the aircraft 15 so that proper corrective action may be taken. Accordingly, indications to the remote server 66 may be communicated from the controller 50 of the system 10 in response to any chemical detection that may be detected by the detection device 12.

In response to the detection (i.e., when a chemical is reported from the detection device 12 to the controller 50), the controller 50 may respond in a variety of ways. For example, in response to the detection of a first chemical, the controller 50 may control a ventilation system 80 to control an air mixing unit that may control a ratio of fresh air entering the aircraft 15 to recirculated air recycled within the aircraft 15. Additionally, the controller 50 may control the activation of an air filtration system 82. In general, the ventilation system 80 may comprise one or more active or passive air filters. For example, the ventilation system 80 may include one or more particulate filters (e.g., a high-efficiency particulate air [HEPA] filter), which may include passive filter media. The air filtration system 82 may further comprise an active filter or air purifier, which may be in connection with an air circulation path or air supply port. Accordingly, in response to a chemical reported, the controller 50 may activate the filtration system 82.

The filtration system 82 may correspond to various types of air filters and/or purifiers. Air purifiers that may be utilized may include active UV-C air filters, ionizers, and other types of filters. Accordingly, the controller 50 may provide for a different response in response to detection of each of a plurality of chemicals in the aircraft 15. Though specific chemicals are discussed in reference to the corrective actions (e.g., ventilation, filtration, etc.), it shall be understood that the controller 50 may be configured to apply various corrective actions alone or in combination based on a desired configuration of the system 10. The controller 50 may additionally activate an alarm or warning, which may be displayed on a screen or indicator corresponding to one or more of the zones 16 of the aircraft 15. In some embodiments, an instruction may be provided by the alarm or alert, which may instruct the flight crew to seek maintenance for the aircraft 15. Accordingly, the system 10 may be configured based on a desired response, which may be tailored to an application, a particular aircraft, geographic region of operation, etc.

In some embodiments, the configuration of the system 10 may be configured based on one or more standard warnings, which may relate to the detection of generally dangerous chemicals. Additionally, the system 10 may be configured to provide custom alerts, detections, or corrective actions based on specific allergies, chemicals, and/or odors that a user indicates as being problematic. For example, if an individual has a specific allergy (e.g. peanuts, tree nuts, soy, etc.), the system may be selectively configured to alert at a user-defined detection level in response to the detection of the chemicals associated with the allergen. The user-defined detection level may correspond to a predetermined concentration or threshold of the associated chemical(s) that if exceeded as a result of the presence of the associated chemicals, the controller 50 of the system 10 may trigger the alert or notification of the detection. In this way, the system 10 may provide for customized controls to assign alerts in response to any chemicals that may be detected by the detection device 12.

In one aspect of the disclosure, a detection system for an aircraft comprises at least one nanofiber chemical sensor for sensing an airborne material. The nanofiber chemical sensor has an electrical characteristic that changes in the presence of the airborne material. The system further comprises a processor coupled to the nanofiber chemical sensor. The processor monitors electrical characteristic of the nanofiber chemical sensor and generates a detection signal in response to a change in the electrical characteristic.

According to various aspects of the disclosure, the detection system may include one or more of the following features or configurations:
- a controller and a plurality of chemical sensor modules, each of the chemical sensor modules comprising at least one of the nanofiber chemical sensors;
- the plurality of chemical sensors is distributed in a plurality of compartments or zones in the aircraft;
- the controller is configured to receive detection signals from the plurality of chemical sensor modules indicating a chemical presence in each of the plurality of compartments or zones in the aircraft;
- the controller is configured to, in response to the detection, output a status indication via a status monitor indicating the chemical presence and the corresponding compartments or zones in the aircraft in which the chemical presence is detected;
- the system comprises a plurality of chemical sensors positioned in a plurality of ventilation flows of a ventilation system, each of the ventilation flows associated with one of the plurality of compartments or zones in the aircraft;
- the ventilation flows are received from each of the plurality of compartments or zones in the aircraft and each of the plurality of chemical sensor modules report detection signals indicating a chemical presence in each of the plurality of compartments or zones in the aircraft;
- the at least one nanofiber chemical sensor is an organic conductive nanofiber chemical sensor;
- the at least one nanofiber chemical sensor comprises a plurality of nanofiber chemical sensors coupled to the processor;
- the processor is configured to distinguish among a plurality of airborne materials in response to electrical characteristics detected by the plurality of nanofiber chemical sensors; and/or
- the controller is configured to output a status indication identifying a chemical composition of the airborne material via a status monitor and a corresponding compartment or zone in the aircraft in which the chemical presence is detected.

In another aspect of the disclosure, a method for sensing an airborne material in an aircraft is disclosed. The method comprises monitoring electrical characteristics detected by a plurality of nanofiber chemical sensors forming a plurality of air quality sensors. The plurality of air quality sensors are disposed in a plurality of detections zones distributed throughout the aircraft. The method further comprises sensing an airborne material in one of the detection zones in response to a detection signal communicated from one of the air quality sensors and identifying an affected zone of the plurality of detection zones in which the airborne material is detected in response to the detection signal communicated from one of the air sensors. The method further comprises outputting a status indication identifying the affected zone in response to the identification of the affected zone and the airborne material.

According to various aspects of the disclosure, the detection method may include one or more of the following steps, features, or configurations:
- the plurality of zones comprise a plurality of passenger compartments or storage compartments of the aircraft;
- identifying a composition of the airborne material;
- the composition of the airborne material is identified in response to electrical characteristics detected by the plurality of nanofiber chemical sensors;
- controlling an activation of filtration system in response to the detection signal; and/or
- controlling an air mixing unit to control an adjustment of a fresh air and recirculated air supplied to detection zones in response to the detection signal.

In yet another aspect of the disclosure, a detection system for an aircraft is disclosed. The system comprises a plurality of chemical sensor modules disposed in a plurality of compartments of the aircraft. The plurality of chemical sensor modules includes a plurality of nanofiber chemical sensors configured to distinguish among a plurality of airborne materials in response to electrical characteristics detected by the plurality of nanofiber chemical sensors. A controller is in communication with the chemical sensor modules. The controller is configured to receive detection signals from the plurality of chemical sensor modules indicating a chemical presence in each of the plurality of compartments or zones in the aircraft. In response to the detection, the controller outputs a status indication indicating the chemical presence and the corresponding compartment or zone in the aircraft in which the chemical presence is detected.

According to various aspects of the disclosure, the detection method may include one or more of the following steps, features, or configurations:
- the plurality of chemical sensors are positioned in a plurality of ventilation flows of a ventilation system, each of the ventilation flows associated with one of the plurality of compartments or zones in the aircraft; and/or
- the ventilation flows are received from each of the plurality of compartments or zones in the aircraft and each of the plurality of chemical sensor modules report the detection signals indicating a chemical presence in each of the plurality of compartments or zones in the aircraft.

It will be understood by one having ordinary skill in the art that construction of the described device and other components may not be limited to any specific material. Other exemplary embodiments of the device disclosed herein may be formed from a wide variety of materials unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the device as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structure without departing from the concepts of the present invention, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above are merely for illustrative purposes and not intended to limit the scope of the device, which is defined by the following claims as interpreted according to the principles of patent law, including the Doctrine of Equivalents.

What is claimed is:

1. A detection system for an aircraft comprising:
    a plurality of zones;
    a plurality of ventilation flows of a ventilation system, the ventilation flows associated with at least one of the plurality of zones;
    a plurality of chemical sensors for sensing an airborne material, the chemical sensors having an electrical characteristic that changes in the presence of the airborne material;
    at least one processor coupled to the chemical sensors, wherein the processor monitors the electrical characteristic of the chemical sensor and generates a detection signal in response to a change in the electrical characteristic;
    the at least one processor is configured to:
    receive the detection signal from the plurality of chemical sensors indicating a chemical presence in at least one of the plurality of zones in the aircraft; and
    in response to receiving the detection signal, actively control an air circulation apparatus for at least one of the ventilation flows of the ventilation system, wherein the air circulation apparatus is in connection with an air supply port configured to control a ratio of fresh air to recirculated air drawn to at least one of the plurality of ventilation flows.

2. The system according to claim 1, wherein the processor is configured to:
    in response to the detection, output a status indication via a status monitor indicating the chemical presence and the at least one zone in the aircraft in which the chemical presence is detected; and
    access information from a user profile, wherein the user profile is associated with a passenger or class of passengers, and the information from the user profile comprises a user-defined chemical threshold.

3. The system according to claim 2, wherein the chemical presence in the at least one of the plurality of zones is categorized as a hazardous chemical or a non-hazardous chemical.

4. The system according to claim 3, wherein the controller is further configured to:
    respond to the detection of the hazardous chemical with a first control output of the ventilation system and respond to the detection of the non-hazardous chemical with a second control output of the ventilation system, the second control output different from the first control output.

5. The system according to claim 1, wherein the at least one plurality of chemical sensors comprises a plurality of nanofiber chemical sensors coupled to the processor.

6. The system according to claim 5, wherein the processor is configured to:
    distinguish among a plurality of airborne materials in response to electrical characteristics detected by the plurality of nanofiber chemical sensors; and
    output a status indication identifying a chemical composition of the airborne material in the at least one zone in the aircraft in which the chemical presence is detected.

7. The system according to claim 1, wherein the air control apparatus includes:
    an air filtration system configured to filter the air drawn to the affected zone in which the chemical presence is detected; and
    an air supply port configured to provide a passenger-defined control of a ratio of fresh air to recirculated air, the ratio of fresh air to recirculated air drawn to the ventilation flows associated with the affected passenger zones.

8. The system according to claim 7, wherein the controller is configured to:
    in response to the chemical presence exceeding the user-defined threshold relating to a comfort concern, actuate the passenger-defined control of the air supply port in the corresponding zone; and
    in response to the chemical presence exceeding the user-defined threshold relating to a safety concern, alert the passenger or the class of passengers and actuate the air filtration system to mitigate the safety concern.

9. A method for sensing and tracking an airborne material in an aircraft, the method comprising:

monitoring electrical characteristics detected by a plurality of chemical sensors in a plurality of detection zones distributed throughout the aircraft forming a plurality of air quality sensors;

sensing an airborne material in one or more of the detection zones in response to a detection signal communicated from one or more of the air quality sensors;

identifying instances of detection in a plurality of affected zones of the plurality of detection zones in which the airborne material is detected in response to the detection signal communicated from one of the air sensors;

identifying a plurality of changes in the airborne material among the plurality of affected zones in which the airborne material is detected; and outputting a status indication identifying a spatial distribution among the affected zones in response to the identification of the changes.

10. The method according to claim 9, wherein the plurality of zones comprise a plurality of passenger compartments or storage compartments of the aircraft.

11. The method according to claim 9, further comprising:
controlling an activation of a filtration system in response to the detection signal.

12. The method of claim 9, further comprising:
identifying a temporal relationship among the changes in the airborne material among the plurality of zones.

13. The method of claim 9, further comprising:
identifying at least one affected passenger among the plurality of affected zones.

14. A detection system for an aircraft comprising:
a plurality of passenger detection zones;
a plurality of chemical sensor modules distributed in the plurality of passenger detection zones of the aircraft, the plurality of chemical sensor modules comprising a plurality of nanofiber chemical sensors configured to distinguish among a plurality of airborne materials; and
a controller in communication with the chemical sensor modules, the controller configured to:
receive detection signals from at least one of the plurality of chemical sensor modules indicating a chemical presence in one or more of the plurality of passenger detection zones in the aircraft;
compare a detection level of the chemical presence to a plurality of user-defined thresholds in the plurality of passenger detection zones; and
in response to the detection level exceeding the user-defined threshold, selectively actuate an air control apparatus in an affected zone in which the detection level is exceeded.

15. The system according to claim 14, wherein a plurality of ventilation flows are connected to the air control apparatus and received from each of the plurality of passenger detection zones in the aircraft, and each of the plurality of chemical sensor modules report the detection signals indicating the chemical presence in the affected zone of the plurality of zones in the aircraft to the controller.

16. The system according to claim 15, wherein the controller is configured to:
in response to the detection, output a status indication indicating the chemical presence and the affected zone of the plurality of zones in the aircraft in which the chemical presence is detected;
identify at least a concentration of the chemical presence; and
identify one of the plurality of zones in which the chemical presence originated.

* * * * *